US012642701B2

(12) United States Patent
Preuss et al.

(10) Patent No.: US 12,642,701 B2
(45) Date of Patent: Jun. 2, 2026

(54) SYSTEM, CONTACT DEVICE, AND METHOD FOR PRODUCING A CONTACT DEVICE

(71) Applicant: Carl Zeiss Meditec AG, Jena (DE)

(72) Inventors: Dirk Preuss, Jena (DE); Andreas Wirth, Simbach am Inn (DE)

(73) Assignee: Carl Zeiss Meditec AG, Jena (DE)

( * ) Notice: Subject to any disclaimer, the term of this patent is extended or adjusted under 35 U.S.C. 154(b) by 862 days.

(21) Appl. No.: 17/904,800

(22) PCT Filed: Feb. 24, 2021

(86) PCT No.: PCT/EP2021/054575
§ 371 (c)(1),
(2) Date: Feb. 13, 2023

(87) PCT Pub. No.: WO2021/170664
PCT Pub. Date: Sep. 2, 2021

(65) Prior Publication Data
US 2024/0122759 A1     Apr. 18, 2024

(30) Foreign Application Priority Data

Feb. 28, 2020     (DE) ..................... 10 2020 105 335.5

(51) Int. Cl.
*A61F 9/009*          (2006.01)
*A61B 17/00*          (2006.01)
(52) U.S. Cl.
CPC .... *A61F 9/009* (2013.01); *A61B 2017/00526* (2013.01)
(58) Field of Classification Search
CPC .. A61F 9/009; A61F 2009/0052; A61F 9/008; A61F 9/00802; A61F 9/00804;
(Continued)

(56) References Cited

U.S. PATENT DOCUMENTS 6,421,173 B1     7/2002  Corbisiero et al.
7,244,026 B1 *   7/2007  Ross, III ................ G02B 7/025
351/219
(Continued)

FOREIGN PATENT DOCUMENTS

CN          101175459 A      5/2008
CN          101282699 A     10/2008
(Continued)

OTHER PUBLICATIONS

International Search Report (English translation) and Written Opinion for PCT/EP2021/054575 mailed May 19, 2021.
(Continued)

*Primary Examiner* — Aaron F Roane
(74) *Attorney, Agent, or Firm* — DeWitt LLP

(57)     ABSTRACT

A system including: a contact element for fixing the relative geometric position and orientation of a patient's eye with respect to a laser applicator and a lens element for insertion into the contact element. The contact element receives the lens element at a predetermined position. The lens element has an eye surface and the lens element has a projection element that engages with one or several holding elements from below for fastening the lens element in the contact element by a snap-action connection. The lens element presents a lens contact surface on a lower side of a projection element. The at least one projection element engages the at least one holding element. The lens contact surface is pressed against an elastic compensation element arranged on a fastening surface of the contact element and serving to reduce the forces acting on the lens element by the at least one holding element.

22 Claims, 3 Drawing Sheets

(58) Field of Classification Search
CPC .............. A61F 9/00806; A61F 9/00808; A61F 9/0081; A61F 9/00812; A61F 9/00814; A61F 9/00817; A61F 9/00819; A61F 9/00821; A61F 9/00823; A61F 9/00825; A61F 9/00827; A61F 9/00829; A61F 9/00831; A61F 9/00834; A61F 9/00836; A61F 9/00838; A61F 9/0084; A61B 2017/00526
USPC ............................................................ 606/4
See application file for complete search history.

(56) References Cited

U.S. PATENT DOCUMENTS

| | | |
|---|---|---|
| 2004/0130807 A1 | 7/2004 | Hattori et al. |
| 2007/0173791 A1 | 7/2007 | Raksi |
| 2008/0071254 A1 | 3/2008 | Lummis et al. |
| 2008/0234707 A1 | 9/2008 | Muehlhoff et al. |
| 2013/0102895 A1* | 4/2013 | Gooding ............. A61F 9/00827 600/426 |
| 2014/0216468 A1 | 8/2014 | Goldshleger et al. |
| 2020/0253781 A1 | 8/2020 | Pössel et al. |
| 2021/0259880 A1* | 8/2021 | Newton .............. A61F 9/00745 |
| 2021/0318555 A1 | 10/2021 | Preuss et al. |

FOREIGN PATENT DOCUMENTS

| | | |
|---|---|---|
| DE | 102010022934 A1 | 12/2011 |
| DE | 10 2018 215030 | 3/2019 |
| DE | 102017215589 | 3/2019 |
| JP | 2013248303 | 12/2013 |
| JP | 2016193028 A | 11/2016 |
| JP | 2019076329 A | 5/2019 |
| WO | WO2007022993 | 3/2007 |
| WO | WO2016100439 | 6/2016 |

OTHER PUBLICATIONS

Office Action with Search Report issued with regard to counterpart foreign application and/or related application CN 202180012227.6. Machine Translation of CN 101175459, 12 pages.

* cited by examiner

SYSTEM, CONTACT DEVICE, AND METHOD FOR PRODUCING A CONTACT DEVICE

RELATED APPLICATIONS

This application is a National Phase entry of PCT Application No. PCT/EP2021/054575 filed Feb. 24, 2021, which application claims the benefit of priority to Germany Application No. 10 2020 105 335.5 filed, Feb. 28, 2020, the entire disclosures of which are incorporated herein by reference.

TECHNICAL FIELD

The invention relates to a system, a contact device and a method for producing a contact device.

BACKGROUND

A contact device in the form of a contact glass or in the form of a liquid patient interface is used in an ophthalmological laser therapy system for the purposes of fixing the relative geometric position and orientation of a patient's eye with respect to a laser applicator. In the case of the contact glass or liquid patient interface, an optically active lens element is held in the contact device at a fixed or specified position. To this end, the lens element is frequently fastened in the contact device by use of an adhesive in the prior art.

A disadvantage in this respect is that the production process of fastening the lens element in the contact elements for the purposes of producing the contact device requires much time and has significant staff requirements, or is complicated from a technical point of view. Moreover, this requires special tools and specifically trained staff.

SUMMARY OF THE INVENTION

Example embodiments of the invention include a system and a contact device, which are simple to produce, and a method for producing a contact device, which is simple to carry out, in each case from a technical point of view.

According to an example embodiment, the invention includes a system comprising a contact element for fixing the relative geometric position and orientation of a patient's eye with respect to a laser applicator of an ophthalmological laser therapy system and a lens element for insertion into the contact element, wherein the contact element is configured to receive the lens element at a predetermined position, wherein the lens element comprises an eye surface for contacting the patient's eye or for forming an air-tight boundary of a cavity between the lens element and the patient's eye, wherein the lens element comprises at least one projection element for engaging with one or several holding elements of the contact element from below for fastening the lens element in the contact element by a snap-action connection without the use of an adhesive, wherein the lens element comprises a lens contact surface formed on a lower side of the projection element facing the eye surface, wherein the lens element and the contact element are configured such that the lens element is able to be fastened in the contact element by use of the snap-action connection such that by interaction of the at least one projection element and the one holding element or the several holding elements the lens contact surface is pressed against an elastic compensation element arranged on a fastening surface of the contact element and serving to reduce the forces acting on the lens element by way of the one holding element or the several holding elements.

An advantage of this is that the system is particularly easily producible from a technical point of view and the lens element can be inserted into or fastened in the contact element for the purposes of forming a contact device in a technically simple manner. In particular, the lens element can be inserted into and fastened in the contact element by hand using simple tools with widespread availability to produce the contact device. An automated insertion or fastening is also possible. In particular, no special tools are required for the purposes of fastening the lens element to the contact element for the purposes of producing the contact device. Additionally, the person fastening the lens element into the contact element need not be specially educated or trained from a technical point of view. Hence, a large number of contact devices comprising the contact element and the lens element inserted into the contact element or fastened to the contact element can be produced within a very short time. Moreover, the space required to produce the contact device comprising the contact element and the lens element inserted into the contact element or fastened to the contact element is particularly small. Additionally, the production costs are low. Moreover, an inadvertent adhesive bonding of other elements to one another or an adhesion of an adhesive at unwanted positions is reliably prevented since no adhesive is required to fasten the lens element in the contact element. A change in the optical properties of the lens element is reliably prevented by the compensation element.

According to an example embodiment, the invention includes a contact device for fixing the relative geometric position and orientation of a patient's eye with respect to a laser applicator of an ophthalmological laser therapy system, wherein the contact device comprises a contact element and a lens element, wherein the lens element is securely connected by a snap-action connection to the contact element without the use of an adhesive, wherein the lens element comprises an eye surface for contacting the patient's eye or for forming an air-tight boundary of a cavity between the lens element and the patient's eye, wherein the lens element comprises at least one projection element for engaging with one or several holding elements of the contact element from below for fastening the lens element in the contact element by use of a snap-action connection without the use of an adhesive, wherein the lens element comprises a lens contact surface formed on a lower side of the projection element that faces the eye surface, wherein the lens element is fastened in the contact element by use of the snap-action connection such that by interaction of the at least one projection element and the one holding element or the several holding elements the lens contact surface is pressed against an elastic compensation element arranged on a fastening surface of the contact element and serving to reduce the forces acting on the lens element by way of the one holding element or the several holding elements.

What is advantageous about this is that the contact device is particularly easily producible from a technical point of view. In particular, the lens element can be fastened in the contact element in technically particularly simple fashion. No special or adapted tools are required for producing the contact device. The contact device can be produced in automated or machine-based fashion. For the purposes of producing the contact device, the person fastening the lens element into the contact element need not be specially educated or trained from a technical point of view. Hence, a large number of contact devices comprising the contact element and the lens element inserted into the contact element or fastened to the contact element can be produced within a very short time. Moreover, the space required to produce the contact device comprising the contact element and the lens element inserted into the contact element or fastened to the contact element is particularly small. Additionally, the production costs are low. Moreover, an inadvertent adhesive bonding of other elements to one another or an adhesion of an adhesive at unwanted positions is reliably prevented since no adhesive is required or used to fasten the lens element in the contact element. A change in the optical properties of the lens element is reliably prevented by the compensation element.

According to an example embodiment, the invention includes a method for producing a contact device for fixing the relative geometric position and orientation of a patient's eye with respect to a laser applicator of an ophthalmological laser therapy system, the contact device comprising a contact element and a lens element, and the method comprising the following steps:

providing a contact element with one or several holding elements;

providing a lens element, wherein the lens element comprises an eye surface for contacting the patient's eye or for forming an air-tight boundary of a cavity between the lens element and the patient's eye, wherein the lens element comprises at least one projection element for engaging with the one or the several holding elements of the contact element from below for fastening the lens element in the contact element by a snap-action connection without the use of an adhesive, wherein the lens element comprises a lens contact surface formed on a lower side of the at least one projection element facing the eye surface; and fastening the lens element in the contact element by use of a snap-action connection without the use of an adhesive by virtue of the at least one projection element being latched into place below the holding element or holding elements in such a way that by interaction of the at least one projection element and the one holding element or the several holding elements the lens contact surface is pressed against an elastic compensation element arranged on a fastening surface of the contact element and serving to reduce the forces acting on the lens element by way of the one holding element or the several holding elements.

An advantage of this method is that the method is able to be carried out technically easily and quickly. Furthermore, the method requires little space. Moreover, no specifically adapted tools are required. The staff carrying out the method need not be specifically trained. Consequently, the method is able to be carried out cost-effectively. A change in the optical properties of the lens element is reliably prevented by the compensation element. Moreover, an inadvertent adhesive bonding of other elements to one another or an adhesion of an adhesive at unwanted positions is reliably prevented since no adhesive is used for securely fastening the lens element to the contact element.

According to an embodiment of the system, the lens element and the contact element are configured such that the lens element is able to be fastened in the contact element such that the compensation element is arranged all around the optical axis of the lens element. An advantage of this is that the arising forces are distributed particularly evenly over the lens element and the fastening surface. This prevents negative effects on the optical properties of the lens element even more reliably.

According to an embodiment of the system, the compensation element is configured to seal the region between the lens contact surface and the fastening surface in air-tight fashion. An advantage of this is that a contact device which seals at this point as a liquid patient interface or a contact glass which is sucked on over the entire contact surface is formed or producible in a technically simple manner. Consequently, the compensation element can adopt the function of a sealing element at the same time. It is possible that the lens element is fastenable in the contact element in such a way that the compensation element is not arranged completely all the way around the optical axis of the lens element but nevertheless substantially seals or, in an airtight fashion, substantially seals the region between the lens contact surface and the fastening surface when placed on the patient's eye or when sucked on to the patient's eye. By way of example, as a result of being sucked on to the patient's eye, a part of the lens contact surface can be connected to a part of the fastening surface where no compensation element is present, so that there substantially is a seal or an air-tight seal. The suction system can compensate the cutouts between the spaced-apart compensation elements.

According to an embodiment of the contact device, the lens element is fastened in the contact element such that compensation element is arranged all around the optical axis of the lens element. An advantage of this is that the forces arising in the contact device are distributed particularly evenly over the lens element and the fastening surface, and stresses are avoided. This prevents negative effects on the optical properties of the lens element even more reliably.

According to an embodiment of the system or the contact device, the lens contact surface extends perpendicular to the optical axis of the lens element. An advantage of this is that the forces acting on the lens element can be distributed particularly efficiently and over a large area.

According to an embodiment of the system or the contact device, the fastening surface of the contact element extends perpendicular to the optical axis of the lens element when the lens element is fastened in the contact element. As a result, arising forces can be transferred over a large area and efficiently into the contact element by way of the snap-action connection. This reliably prevents the optical properties of the lens element from changing. Moreover, the compensation element can be in large-area contact with the lens contact surface and the fastening surface when the lens contact surface is arranged parallel to the fastening surface.

According to an embodiment of the system or the contact device, the at least one projection element of the lens element comprises or is a bead running substantially all the way around the optical axis of the lens element or the at least one projection element comprises several projection elements arranged at a distance from one another around the optical axis of the lens. An advantage of a circumferential bead is that the lens element or the system or the contact device is even more easily producible from a technical point of view. Moreover, the holding element or the holding elements can secure the lens element over a particularly large area and can secure the latter at a given position in the case of a circumferential bead. Furthermore, the lens element can be rotated relative to the contact element about the optical axis of the lens element in the case of a circumferential bead. An advantage of several spaced-apart projection elements is that the lens element can be fastened in or inserted into the contact element particularly easily from a technical point of view.

According to an embodiment of the system or the contact device, the compensation element has a substantially annular form in a cross section perpendicular to the optical axis of the lens element when the lens element is fastened in the contact element. An advantage of this is that the compensation element is arrangeable particularly easily from a technical point of view. This reduces the production costs and reduces the time required for production. Moreover, the forces can be transferred particularly uniformly from the lens element into the compensation element. This prevents possible negative effects on optical properties of the lens element even more reliably.

According to an embodiment of the system or the contact device, the contact element comprises several holding elements which are arranged at a distance from one another, in particular equidistantly from one another, around the optical axis of the lens when the lens element is fastened in the contact element. An advantage of this is that the lens element can be inserted into the contact element in technically simple fashion. Moreover, no large forces are applied to the lens element when the lens element is inserted into the contact element or when the snap-action connection is produced, and so a change of the optical properties of the lens element is also reliably prevented during the insertion into the contact element.

According to an embodiment of the system or the contact device, the one or the several holding elements of the contact element has/have such a resilient form that the one or the several holding elements is/are configured to be mechanically movable for the purposes of latching the at least one projection of the lens element below the holding element or the holding elements for the purposes of forming the snap-action connection. As a result, the lens element can be inserted into the contact element easily from a technical point of view, in particular by hand. Moreover, only small forces act on the lens element during the insertion of the lens element into the contact element. This reliably prevents a (permanent) changing of the optical properties of the lens element.

According to an embodiment of the system or the contact device, the compensation element has a marking and/or color assigned to the respective design of the contact device. An advantage of this is that a person can optically quickly and reliably distinguish between different designs of the contact device. This reliably avoids an incorrect use or incorrect selection of the contact device. Different designs of the contact device may for example comprise a different lens element but the same design of contact element in each case.

According to an embodiment of the method, the lens contact surface extends perpendicular to the optical axis of the lens element. This is advantageous in that the forces acting on the lens element are distributed particularly efficiently and over a large area.

According to an embodiment of the method, the contact element comprising the flexible compensation element is produced by a multi-component injection molding method, in particular a two-component injection molding method. What is advantageous about this is that the contact device is easily, quickly, and cost-effectively producible from a technical point of view. Moreover, this requires no additional work step for arranging the compensation element.

According to an embodiment of the method, the one or the several holding elements of the contact element is/are mechanically reversibly moved, in particular away from the optical axis of the lens element, for the purposes of inserting a part of the at least one projection of the lens element between the holding element or the holding elements of the contact element and the fastening surface of the contact element for the purposes of forming the snap-action connection. An advantage of this is that the lens element is able to be inserted into the contact element in a technically simple fashion, in particular by hand. Moreover, only small forces act on the lens element during the insertion. This reliably prevents a (permanent) changing of the optical properties of the lens element.

According to an embodiment of the method, the at least one projection element of the lens element comprises a bead running substantially all the way around the optical axis of the lens element. An advantage of this is that the contact device is producible even more easily from a technical point of view. Additionally, the lens element is secured over a particularly large area by the holding element or the holding elements and held at a specified position. Moreover, a rotation of the lens element relative to the contact element about the optical axis of the lens element does not change the fastening of the lens element in the contact element.

It is also conceivable for the contact element to have one or more cutouts into which the compensation element is at least partly pressed when the lens element is inserted into the contact element and into which the compensation element can be partly diverted as it were. This even further reduces the forces acting on the lens element.

BRIEF DESCRIPTION OF THE DRAWINGS

The invention is explained in greater detail below with reference to drawings of exemplary embodiments. In the figures.

The same reference signs are used in the following description for identical parts and parts having an identical effect.

DETAILED DESCRIPTION

Figure 1:
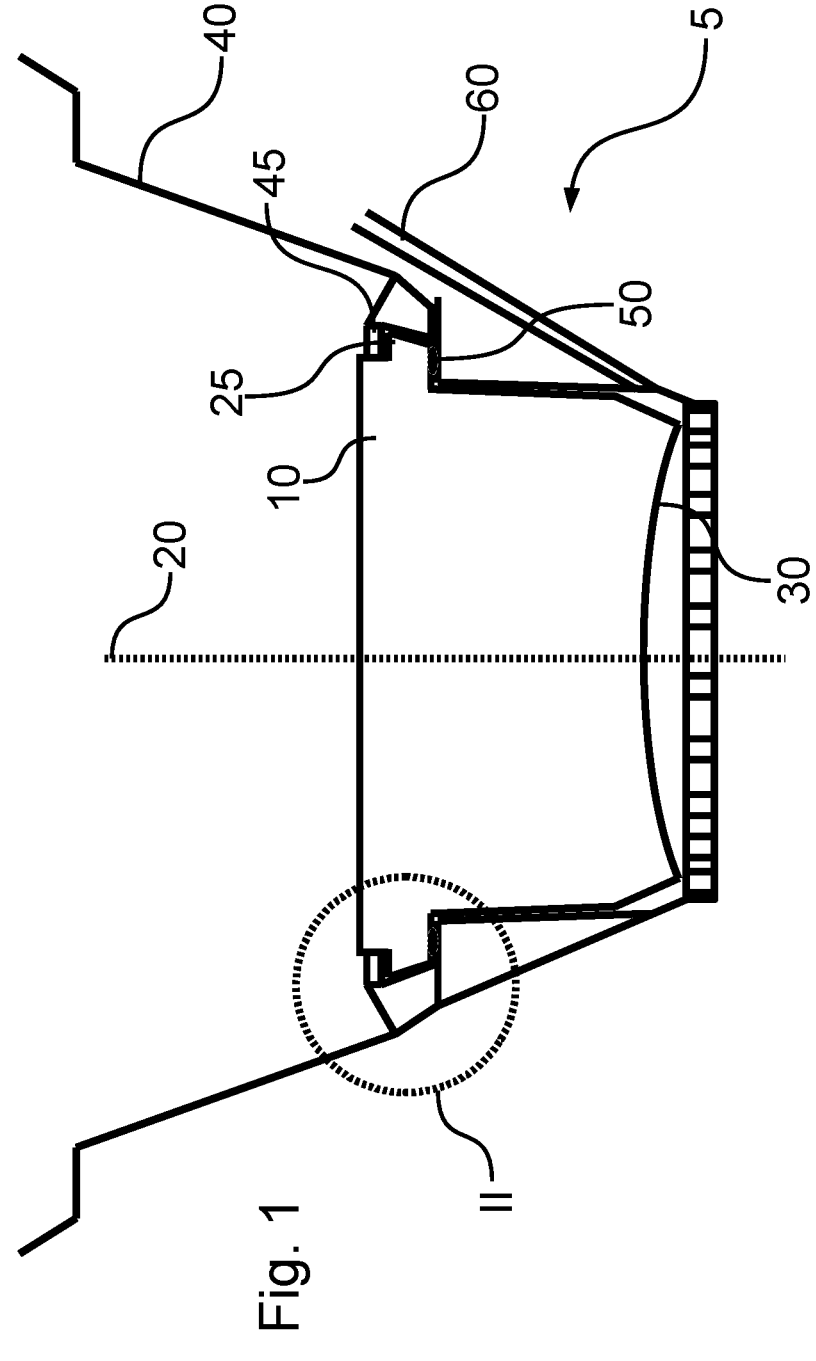
FIG. 1 depicts a schematic side view of an embodiment of the contact device according to the invention.
Figure 2:
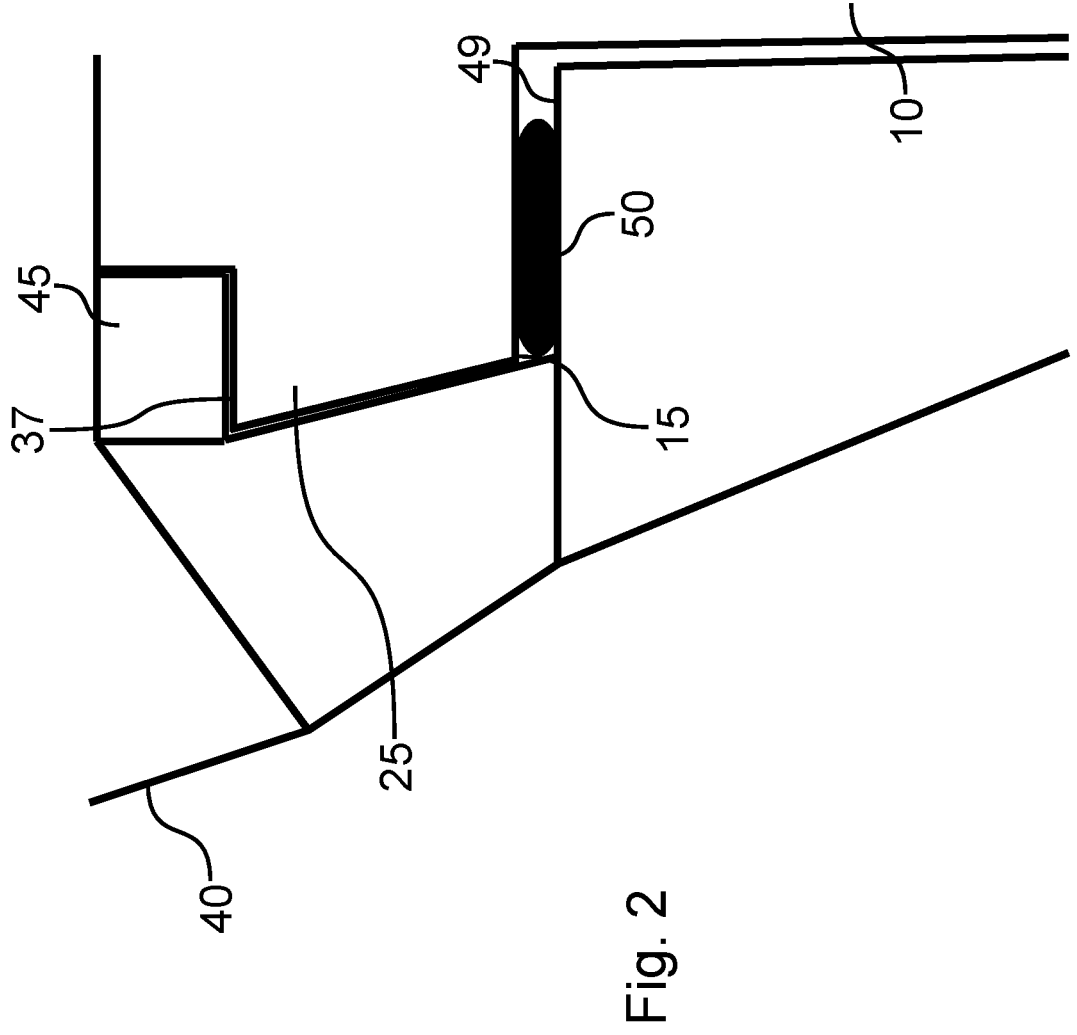
FIG. 2 depicts a detailed view of region II in FIG. 1.
Figure 3:
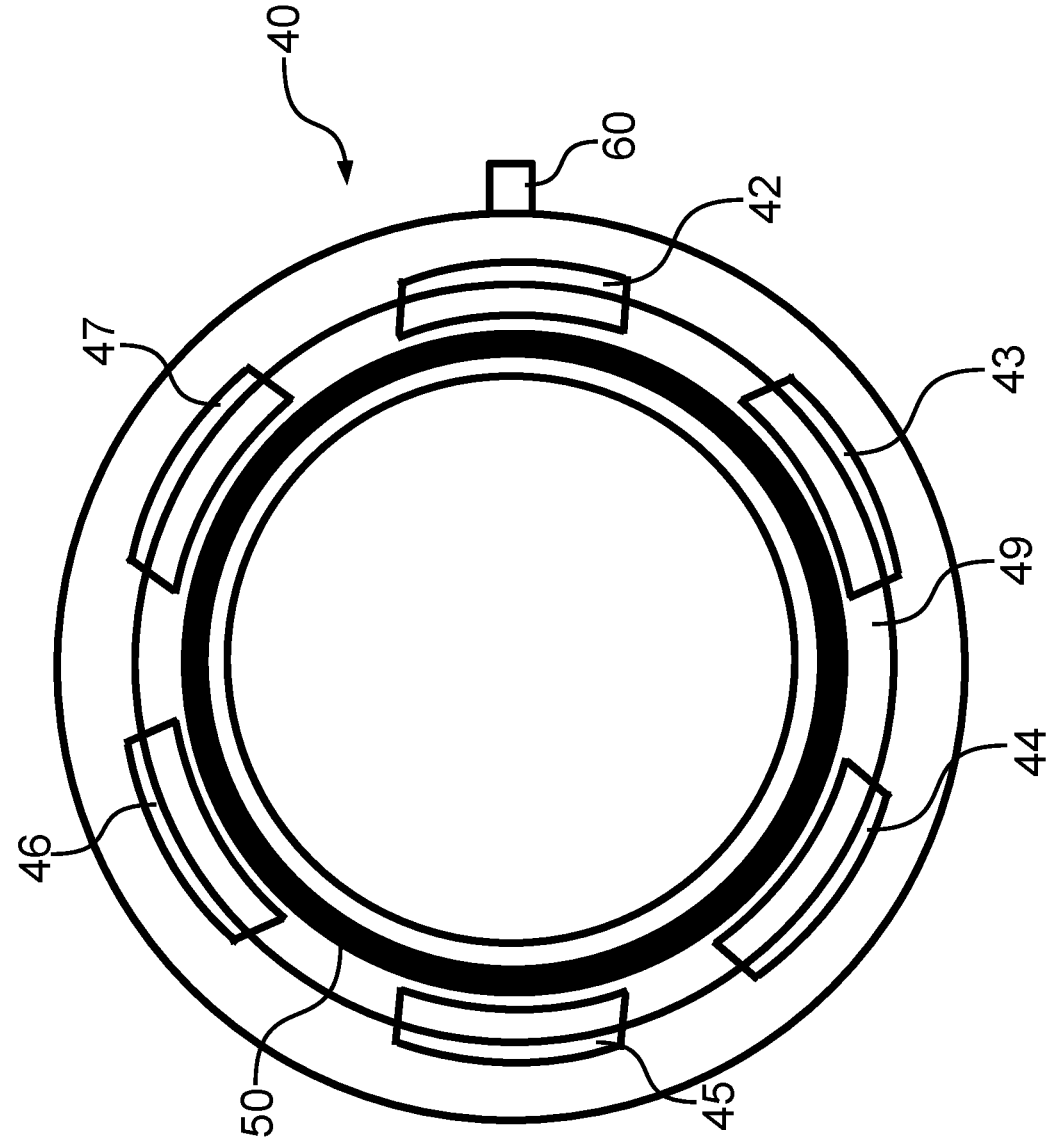
FIG. 3 depicts a plan view of the contact element of the contact device from FIG. 1 and FIG. 2.

FIG. 1 depicts a schematic side view of an embodiment of the contact device 5 according to the invention. FIG. 2 shows a detailed view of region II in FIG. 1. FIG. 3 a plan view of the contact element 40 of the contact device 5 from FIG. 1 and FIG. 2 from above, that is to say in the direction of the light beam during the treatment of the patient's eye.

The contact device 5 is configured to fix the relative geometric position and orientation of a patient's eye with respect to a laser applicator of an ophthalmological laser therapy system. Consequently, the contact device 5 fixes the position of the eye in relation to the laser radiation during the treatment with laser radiation. The contact device 5 is rigidly/securely fastened to the laser therapy system.

The contact device 5 comprises a lens element 10 that is fastened by a snap-action connection and without an adhesive into the contact element 40 of the contact device 5, at or in a specified position.

The contact device 5 can be a contact glass holding device (colloquially also simply referred to as "contact glass"), in the case of which the lens element 10 touches the eye or the cornea. It is possible for the contact device 5 to be a liquid patient interface, in the case of which a cavity between the lens element 10 and the patient's eye is filled with a buffered salt solution (BSS). The salt solution permits adjustment of the refractive index between the lens element 10 and the patient's eye. A liquid patient interface can be used in particular when focusing the laser radiation on lower lying structures in the patient's eye.

The lens element 10 is fastened or arranged securely or at a given position in the contact element 40 of the contact device 5. This means that the relative position between the lens element 10 and the contact element 40 is substantially unchangeable.

The lens element 10 is securely inserted in the contact element 40 by a snap-action connection or click-in connection, that is to say securely connected to the contact element 40 or fastened in the contact element 40. The snap-action connection forms a form fit.

The optical axis 20 of the lens element 10 runs centrally through the lens element 10, that is to say from top to bottom in FIG. 1 and FIG. 2. In FIG. 3, the optical axis 20 of the lens element 10 runs perpendicular to the plane of the drawing if the lens element 10 is fastened to the specified position in the contact element 40.

To establish the snap-action connection between the lens element 10 and the contact element 40, the lens element 10 comprises a projection element 25, for example in the form of an all-around bead, or several projection elements 25. The several projection elements 25 can be formed spaced apart from one another in the circumferential direction about the optical axis 20. By way of example, the several projection elements 25 can be spaced apart equidistantly from one another in the circumferential direction about the optical axis 20. Thus, for example, six projection elements 25, which each extend through 30° of the full circle or circumference, may each have a spacing of 30° from one another in the circumferential direction. Other embodiments of projection elements 25 are conceivable.

The contact element 40 has a conical frustum-shaped outer form. On its inner side, the contact element 40 comprises a holding element 42 or several holding elements 42-47. The holding element 42 or the holding elements 42-47 are configured in the form of projections to the inside or toward the optical axis 20 of the lens element 10.

The holding element 42-47 can be configured to completely run around the optical axis 20 of the lens element 10, that is to say extend over the full circle about the optical axis 20 of the lens element 10. Alternatively, it is possible for several holding elements 42-47 to be arranged spaced apart from one another, for example equidistantly spaced apart from one another circumferentially. Like the projection elements 25, the holding elements 42-47 can each extend over a circular arc segment, for example over 35° of the circumference. Alternatively, three holding elements 42-47 may also be present, which are each arranged offset by 120° from one another circumferentially.

The contact element 40 has a fastening surface 49. On the side facing the eye, the lens element 10 has a lens contact surface 15. The lens contact surface 15 can extend perpendicular to the optical axis 20 of the lens element 10. The fastening surface 49 can be configured perpendicular to the optical axis 20 of the lens element 10. Once the lens element 10 has been inserted into the contact element 40 and fastened by operation of the snap-action connection, the lens contact surface 15 and the fastening surface 49 extend parallel to one another.

The lens element 10 has been fastened in the holding element 42-47 in adhesive-free fashion or without using an adhesive. In particular, there is no adhesive between the lens contact surface 15 and the fastening surface 49.

The lens element 10 is fastened in the contact element 40 by virtue of the projection element 25 or the projection elements of the lens element 10 being inserted below the holding element 42-47 or the holding elements 42-47 of the contact element 40 and snapping into place. To this end, the projection elements 25 or the holding elements 42-47 may be reversibly mechanically movable. In particular, the projection elements 25 and/or the holding elements 42-47 can be reversibly movable away from or toward the optical axis 20 of the lens element 10. As a result of inserting the projection element 25 or the projection elements 25 below the holding element 42-47 or the holding elements 42-47, the snap-action connection or the click-in connection is formed between the lens element 10 and the contact element 40. Consequently, a form-fit which substantially prevents a movement of the lens element 10 vis-à-vis the contact element 40 is formed between holding element 42-47 and projection element 25.

The projection element 25 is held between the holding element 42-47 or the holding elements 42-47 and the fastening surface 49. The projection element 25 and the holding element 42-47 press the lens contact surface 15 in the direction of the fastening surface 49.

An elastic compensation element 50 is arranged on the fastening surface 49. The compensation element 50 has an elastic embodiment, that is to say the compensation element 50 subsequently seeks to readopt its original form. The compensation element 50 may comprise a plastic or consist of plastic. By way of example, the compensation element 50 consists of a rubber plastic.

It is possible but not mandatory that a cutout or depression for receiving a part of the compensation element 50 is formed in the fastening surface 49. The compensation element 50 can be arranged particularly precisely in this manner.

The compensation element 50 can have a ring-shaped embodiment in a cross sectional plane extending at right angles to the optical axis 20 of the lens element 10. The compensation element 50 can have a toroidal embodiment, similar to that of an O-ring. Other shapes are possible. For example, it can have a donut shape.

The compensation element 50 can be configured to completely run around the optical axis 20 of the lens element 10.

The compensation element 50 can have an air-tight form. As a result, the region between the lens contact surface 15 and the fastening surface 49 can be sealed in air-tight fashion. This is particularly important in the case of a liquid patient interface since the cavity here, the cavity delimited by the eye surface 30 of the lens element 10, should be tightly sealed between lens element 10 and the patient's eye. This is also important in the case of a contact element embodied as a contact glass and sucked-on over the entire contact surface with the eye. However, it is also possible, for example in the case of an embodiment as a liquid patient interface, for an additional suction ring to be present, for example on the external circumference or near the external circumference of the contact element 40, with the suction ring being configured for sucking on to the patient's eye and consequently for the relative fixation of the contact element 40 vis-à-vis the patient's eye. By way of example, no airtight seal of the cavity between lens element 10 and the patient's eye is required in the case of an additional suction ring.

It is also conceivable for the compensation element 50 to have several spaced apart segments, which are spaced apart from one another in the circumferential direction, in particular equidistantly, over the circumference of the fastening surface 49. By way of example, a segment of the compensation element 50 is situated at 6 points of the fastening surface 49. The various segments of the compensation element 50 typically have the same elasticity. In the case of several spaced apart segments of the compensation element 50 or in the case of several spaced apart compensation elements, it is conceivable that a sealing closure or an airtight closure of the region is formed between the lens contact surface 15 and the fastening surface 49 as a result of the pressure of the lens contact surface 15 against the fastening surface 49.

The contact element 40 has an at least partly complementary form to the lens element 10, in particular in such a way that a lateral movement, that is to say a movement perpendicular to the optical axis 20 of the lens element 10, is substantially impossible if the lens element 10 is securely connected to the contact element 40 or fastened in the contact element 40 by use of the snap-action connection. Thus, there is a snug fit in the lateral direction or sideways direction. Consequently, forces do not continually act on the lens element 10 in the lateral direction or sideways direction.

However, it is also conceivable for a further compensation element 50 to be arranged in the lateral direction between the lens element 10 and the contact element 40. The further compensation element 50 can run around the optical axis 20 of the lens element 10 over the full circle or only consist of individual circular segments or arc segments.

As it were, the compensation element 50 is clamped between the lens contact surface 15 and the fastening surface 49. It is conceivable for the compensation element 50 to cover the majority, in particular more than 90%, of the lens contact surface 15 and/or of the fastening surface 49.

The compensation element 50 prevents forces that are too high from acting on the lens element 10 or prevents stresses which could change the optical properties of the lens element 10 from arising in the lens element 10. The compensation element 50 prevents the lens contact surface 15 from pressing directly against the fastening surface 49.

The compensation element 50 comprises no adhesive and implements no adhesive function.

The compensation element 50 is deformed as a result of pressing the lens element 10 or the lens contact surface 15 in the direction of the fastening surface 49. On account of its elasticity, the compensation element 50 presses accordingly against the lens contact surface 15. This prevents a movement of the lens element 10 parallel to the optical axis 20. The compensation element 50 therefore represents a type of buffer between lens contact surface 15 and fastening surface 49 which can absorb forces as a result of deformation such that usually no direct or immediate contact is established between the substantially non-deformable lens contact surface 15 and the substantially non-deformable fastening surface 49.

The contact element 40 with the compensation element 50 can be produced by injection molding methods. In particular, the contact element 40 may be produced by use of a 2-component injection molding method. The contact element 40 without the compensation element 50 may consist of, or be produced from, a first component and the compensation element 50 may consist of, or be produced from, a second component, with the second component differing from the first component. The second component may comprise or be an elastic or flexible plastic or plastic mixture.

A therapy system surface 37 located opposite the eye surface 30 is formed parallel to the eye surface 30. The therapy system surface 37 touches or contacts the holding element 42-47 of the contact element 40. There is a form fit between the therapy system surface 37 and the holding element 42-47. In FIG. 1 and FIG. 2, the therapy system surface 37 cannot move upward since the therapy system surface 37 abuts against the holding element 42-47 of the contact element 40.

The therapy system surface 37 can face away from the eye surface 30. This means that the eye surface 30 points downward in FIG. 1 and FIG. 2 while the therapy system surface 37 points upward or is formed on the upper side of the projection of the lens element 10. The lens contact surface 15 is formed on the lower side of the projection of the lens element 10.

The lens element 10 is inserted into the contact element 40 for the purposes of forming the contact device 5 by virtue of reversibly mechanically moving one or more holding elements 42-47. By way of example, one holding element or several holding elements 42-47 may be partially bent laterally or sideways and/or parallel to the optical axis 20 of the lens element 10 in order to move the projection element 25 or the projection elements under the holding element 42-47 or the holding elements 42-47. Subsequently, the holding element 42-47 or the holding elements 42-47 move or snap back into their original position(s). Now an interlocking snap-action connection is formed between lens element 10 and contact element 40. The projection element 25 or the projection elements of the lens element 10 now is/are situated between the holding element 42-47 or the holding elements 42-47 and the fastening surface 49. The compensation element 50 is arranged between the projection element 25 and the fastening surface 49.

It is also conceivable that a projection element 25 or several projection elements of the lens element 10 are mechanically reversibly moved in order to insert the lens element 10 into the contact element 40 and in order to fasten said lens element in the contact element 40 by use of the snap-action connection or click-in connection.

The snap-action connection typically cannot be released from the contact element 40 in non-destructive fashion.

The lens element 10 has not yet been inserted into the contact element 40 in FIG. 3. It is possible that the entire contact device 5 has no adhesive or no adhesive connection.

The contact device 5 may comprise a suction channel 60 for bringing the eye close by suction.

LIST OF REFERENCE NUMERALS

5 Contact device
10 Lens element
15 Lens contact surface
20 Optical axis of the lens
25 Projection element
30 Eye surface
37 Therapy system surface
40 Contact element
42-47 Holding element
49 Fastening surface
50 Compensation element
60 Suction channel

The invention claimed is:

1. A system, comprising:

a contact element that fixes a relative geometric position and orientation of a patient's eye with respect to a laser applicator of an ophthalmological laser therapy system; and a lens element insertable into the contact element;

wherein the contact element is configured to receive the lens element at a predetermined position;

wherein the lens element comprises an eye surface configured to contact the patient's eye or to form an air-tight boundary of a cavity between the lens element and the patient's eye;

wherein the lens element comprises at least one projection element configured to engage with one or several holding elements of the contact element from below for fastening the lens element in the contact element by operation of a snap-action connection without the use of an adhesive;

wherein the lens element comprises a lens contact surface formed on a lower side of the projection element facing the eye surface; and wherein the lens element and the contact element are configured such that the lens element is fastenable in the contact element by operation of the snap-action connection such that by interaction of the at least one projection element and the one holding element or the several holding elements the lens contact surface is pressed against an elastic compensation element arranged on a fastening surface of the contact element and the elastic compensation element serving to reduce forces acting on the lens element by way of the one holding element or the several holding elements.

2. The system as claimed in claim 1, wherein the lens element and the contact element are configured such that the lens element is fastenable in the contact element such that the compensation element is arranged all around an optical axis of the lens element.

3. The system as claimed in claim 1, wherein the compensation element is configured to seal a region between the lens contact surface and the fastening surface in an air-tight fashion.

4. The system as claimed in claim 1, wherein the lens contact surface extends perpendicular to the optical axis of the lens element.

5. The system as claimed in claim 1, wherein the fastening surface of the contact element extends perpendicular to the optical axis of the lens element when the lens element is fastened in the contact element.

6. The system as claimed in claim 1, wherein the at least one projection element of the lens element comprises a bead running substantially all the way around the optical axis of the lens element or the at least one projection element comprises several projection elements arranged at a distance from one another around the optical axis of the lens.

7. The system as claimed in claim 1, wherein the compensation element has a substantially annular form in a cross section perpendicular to the optical axis of the lens element when the lens element is fastened in the contact element.

8. The system as claimed in claim 1, wherein the contact element comprises several holding elements which are arranged at a distance from one another or equidistantly from one another, around the optical axis of the lens when the lens element is fastened in the contact element.

9. The system as claimed in claim 1, wherein the one or the several holding elements of the contact element have such a resilient form that the one or the several holding elements is/are configured to be mechanically movable for the purposes of latching the at least one projection of the lens element below the holding element or the holding elements for the purposes of forming the snap-action connection.

10. The system as claimed in claim 1, wherein the compensation element has a marking, a color or both assigned to the respective design of the contact device.

11. A contact device that fixes a relative geometric position and orientation of a patient's eye with respect to a laser applicator of an ophthalmological laser therapy system, wherein the contact device comprises:

a contact element; and a lens element;

wherein the lens element is securely connected by operation of a snap-action connection to the contact element without the use of an adhesive;

wherein the lens element comprises an eye surface that contacts the patient's eye or that forms an air-tight boundary of a cavity between the lens element and the patient's eye;

wherein the lens element comprises at least one projection element that engages with one or several holding elements of the contact element from below for fastening the lens element in the contact element by operation of a snap-action connection without the use of an adhesive;

wherein the lens element comprises a lens contact surface formed on a lower side of the projection element that faces an eye surface; and wherein the lens element is fastened in the contact element by the operation of the snap-action connection such that by interaction of the at least one projection element and the one holding element or the several holding elements the lens contact surface is pressed against an elastic compensation element arranged on a fastening surface of the contact element and serving to reduce the forces acting on the lens element by way of the one holding element or the several holding elements.

12. The contact device as claimed in claim 11, wherein the lens element is fastened in the contact element such that the compensation element is arranged all around an optical axis of the lens element.

13. The contact device as claimed in claim 11, wherein the lens contact surface extends perpendicular to the optical axis of the lens element.

14. The contact device as claimed in claim 11, wherein the fastening surface of the contact element extends perpendicular to the optical axis of the lens element when the lens element is fastened in the contact element.

15. The contact device as claimed in claim 11, wherein the at least one projection element of the lens element comprises a bead running substantially all the way around the optical axis of the lens element or the at least one projection element comprises several projection elements arranged at a distance from one another around the optical axis of the lens.

16. The contact device as claimed in claim 11, wherein the compensation element has a substantially annular form in a cross section perpendicular to the optical axis of the lens element when the lens element is fastened in the contact element.

17. The contact device as claimed in claim 11, wherein the contact element comprises several holding elements which are arranged at a distance from one another or equidistantly from one another, around the optical axis of the lens when the lens element is fastened in the contact element.

18. The contact device as claimed in claim 11, wherein the one or the several holding elements of the contact element have such a resilient form that the one or the several holding elements is/are configured to be mechanically movable for the purposes of latching the at least one projection of the lens element below the holding element or the holding elements for the purposes of forming the snap-action connection.

19. The contact device as claimed in claim 11, wherein the compensation element has a marking, a color or both assigned to the respective design of the contact device.

20. A method of producing a contact device that fixes the relative geometric position and orientation of a patient's eye with respect to a laser applicator of an ophthalmological laser therapy system, the contact device comprising a contact element and a lens element, and the method comprising:

providing the contact element with one or several holding elements;

providing the lens element;

wherein the lens element comprises an eye surface configured to contact the patient's eye or configured to form an air-tight boundary of a cavity between the lens element and the patient's eye;

wherein the lens element comprises at least one projection element configured to engage with the one or the several holding elements of the contact element from below for fastening the lens element in the contact element by operation of a snap-action connection without the use of an adhesive;

wherein the lens element comprises a lens contact surface formed on a lower side of the at least one projection element facing the eye surface; and fastening the lens element in the contact element by operation of the snap-action connection without the use of the adhesive by virtue of the at least one projection element being latched into place below the holding element or the holding elements in such a way that by means of the at least one projection element and the one holding element or the several holding elements the lens contact surface is pressed against an elastic compensation element arranged on a fastening surface of the contact element and serving to reduce the forces acting on the lens element by way of the one holding element or the several holding elements.

21. The method as claimed in claim 20, wherein further comprising producing the contact element comprising the flexible compensation element by application of a multi-component injection molding method.

22. The method as claimed in claim 20, wherein the one or the several holding elements of the contact element are mechanically reversibly moved, in particular away from the optical axis of the lens element, for the purposes of inserting a part of the at least one projection of the lens element between the holding element or the holding elements of the contact element and the fastening surface of the contact element for the purposes of forming the snap-action connection.

* * * * *